US00PP34314P2

(12) United States Plant Patent
de Gruyter

(10) Patent No.: US PP34,314 P2
(45) Date of Patent: Jun. 7, 2022

(54) ***HELLEBORUS* PLANT NAMED 'GRUHEL02'**

(50) Latin Name: *Helleborus niger*
Varietal Denomination: GRUHEL02

(71) Applicant: Hortimarket B.V., 's-Gravenzande (NL)

(72) Inventor: André de Gruyter, Rockanje (NL)

(73) Assignee: HORTIMARKET B.V., 's-Gravenzande (NL)

( * ) Notice: Subject to any disclaimer, the term of this patent is extended or adjusted under 35 U.S.C. 154(b) by 0 days.

(21) Appl. No.: 17/515,203

(22) Filed: Oct. 29, 2021

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — Penny J. Aguirre

(57) ABSTRACT

A new cultivar of *Helleborus* plant named 'GRUHEL02' that is characterized by its shiny leaves, its healthy foliage, its large flowers, its floriferous and uniform flowering habit with multiple flowers blooming at once, its compact plant habit, its thick leaves and stems, its flowers that are held just above the foliage, its tolerance to heat and stability in warm conditions in The Netherlands, and its suitability for greenhouse growing without issues.

2 Drawing Sheets

Botanical classification: *Helleborus niger.*
Varietal denomination: 'GRUHEL02'.

CROSS-REFERENCE TO A RELATED APPLICATION

This application is related to a European plant breeders' rights application filed on Nov. 30, 2017, application No. 2017/3134. There have been no offers for sale anywhere in the world prior to the effective filing date of this Application and no accessibility to one of ordinary skill in the art could have been derived from the printed plant breeder's rights documents.

The present invention relates to a new and distinct cultivar of *Helleborus* plant, botanically known as *Helleborus niger* 'GRUHEL02', and will be referred to hereinafter by its cultivar name, 'GRUHEL02'. The new cultivar of *Helleborus* is an evergreen perennial grown for landscape and container use.

The new invention arose as part of an ongoing breeding project by the Inventor in Rockanje, The Netherlands. The objectives of the breeding include obtaining new cultivars of *Helleborus* that exhibit early flowering habits, uniformity in growth, stability to stress, large flowers, a floriferous habit, pure white flowers with undulate petal margins.

The new cultivar of *Helleborus*, 'GRUHEL02', arose from a cross made in December of 2000 between unnamed and unpatented proprietary plants from the Inventor's breeding program. The female parent was pollinated with a mixture of pollen and the exact male parentage is therefore unknown. 'GRUHEL02' was selected as a single unique plant in 2013 from the above cross.

Asexual propagation of the new cultivar was first accomplished by the Inventor by tissue culture using meristematic tissue in Rockanje, The Netherlands in 2016. Asexual propagation by tissue culture has been determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRUHEL02' as a unique cultivar of *Helleborus*.

1. 'GRUHEL02' exhibits shiny leaves.
2. 'GRUHEL02' exhibits healthy foliage.
3. 'GRUHEL02' exhibits large flowers.
4. 'GRUHEL02' exhibits a floriferous and uniform flowering habit with multiple flowers blooming at once.
5. 'GRUHEL02' exhibits a compact plant habit.
6. 'GRUHEL02' exhibits thick leaves and stems.
7. 'GRUHEL02' exhibits flowers that are held just above the foliage.
8. 'GRUHEL02' exhibits tolerance to heat and stability in warm conditions in The Netherlands.
9. 'GRUHEL02' exhibits suitability for greenhouse growing without issues.

The female parent of 'GRUHEL02' differs from 'GRUHEL02' in having an uneven and less floriferous blooming habit and flowers that are smaller in size, and in not being suitable for growing a full cycle in a greenhouse. 'GRUHEL02' can be most closely compared to the *Helleborus niger* cultivars 'HGC Jacob' (U.S. Plant Pat. No. 17,799) and 'COSEH210' (U.S. Plant Pat. No. 21,048). 'HGC Jacob' and 'COSEH210' are both similar to 'GRUHEL02' in flower size. 'HGC Jacob' differs from 'GRUHEL02' in having shorter petioles, bracts and nectary that are lighter green in color, and anthers that are more yellow in color. 'COSEH210' differs from 'GRUHEL02' in having shorter petioles that are darker green in color and nectary that are lighter green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by RHS gardening and the Official Gazette of the Community Plant Variety Office.

BRIEF DESCRIPTION OF THE DRAWINGS

The accompanying color photographs illustrates the overall appearance and distinct characteristics of the new *Helleborus*. The photographs were taken of a plant about 8 months in age as grown in a greenhouse in a 11-cm container in 's-Gravenzande, The Netherlands.

The photograph in FIG. 1 provides a side view of the plant habit of 'GRUHEL02' in bloom.

Figure 1:
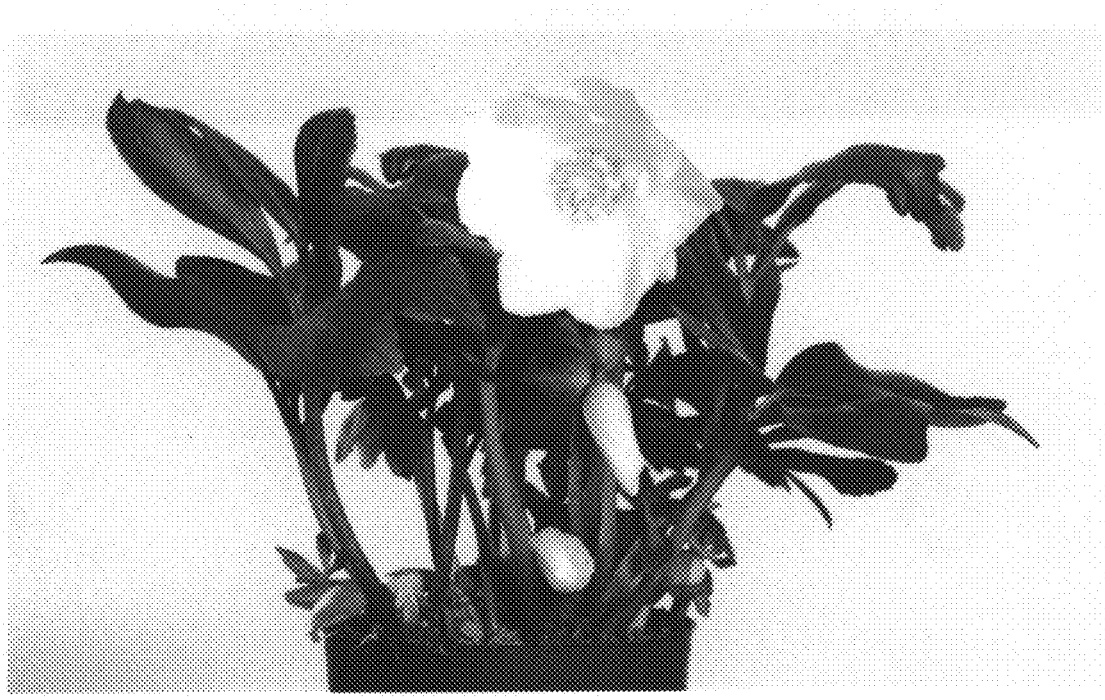
Figure 2:
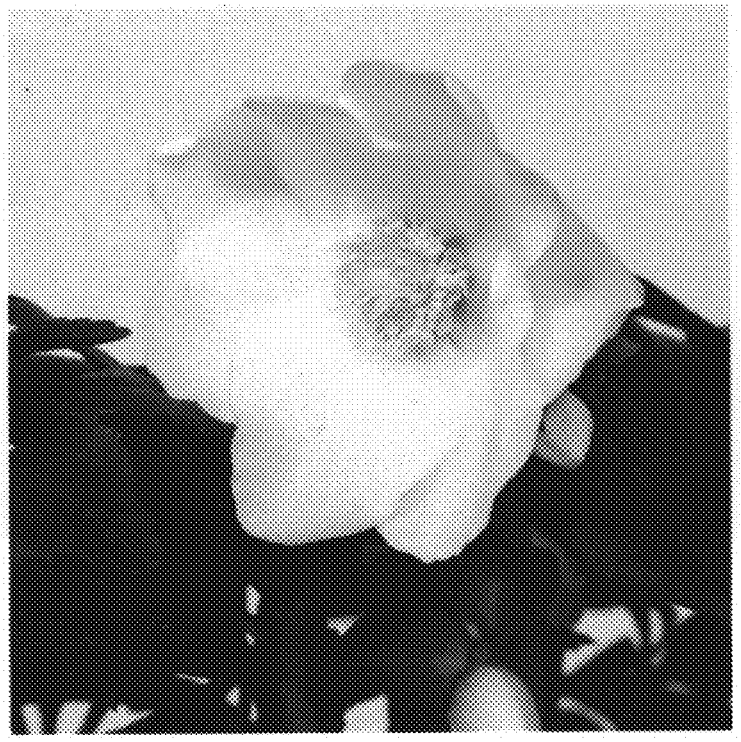

The photograph in FIG. 2 provides a close-up view of the flowers of 'GRUHEL02'.

Figure 3:
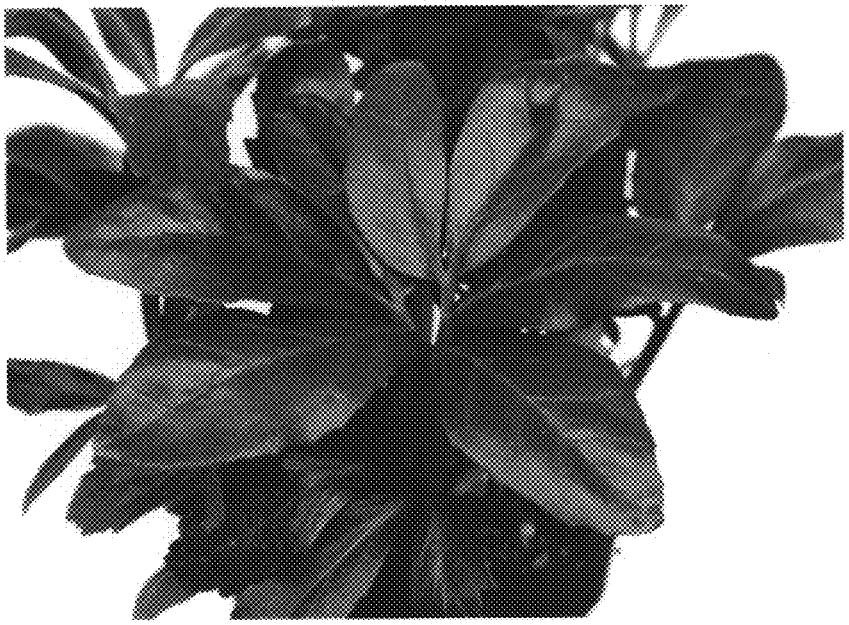

The photograph in FIG. 3 provides a close-up view of the foliage of 'GRUHEL02'.

The colors in the photographs may differ slightly from the color values cited in the detailed botanical description, which accurately describe the colors of the new *Helleborus*.

BOTANICAL DESCRIPTION OF THE PLANT

The following is a detailed description of plants of 'GRUHEL02' about 8 months in age of as grown in a greenhouse in 11-cm containers in 's-Gravenzande, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—3 to 4 weeks in November in The Netherlands.

*Plant type.*—Evergreen perennial.

*Plant habit.*—Compact, upright spreading.

*Height and spread.*—Reaches 25 to 30 cm in height and 15 to 20 cm in spread as grown in a 11-cm container.

*Hardiness.*—At least to U.S.D.A. Zones 3 to 8.

*Diseases and pests.*—No resistance or susceptibility to diseases or pests has been is known, observed to be healthy when greenhouse grown.

*Root description.*—Fine and fibrous, NN155B in color.

*Propagation.*—Tissue culture.

*Growth rate.*—Moderate to high.

*Root development.*—About 10 to 14 days from phase 4 tissue to root in a plug, about 10 to 12 weeks to fully root in a 5-cm plug, about 8 to 9 months to produce a finished plant.

*Branching habit.*—Flowering stems emerge from basal rosettes, an average of 10 stems per plant, no lateral branches.

Foliage description:

*Leaf shape.*—Palmate, orbicular to reniform in outline, lowest leaflets free to strongly overlapping.

*Leaf arrangement.*—Rosette.

*Leaf division.*—Compound.

*Leaf base.*—Attenuate, winged.

*Leaf apex.*—Bluntly acute.

*Leaf margins.*—Serrate to coarsely serrate, slightly coarsely undulate to moderately coarsely undulate.

*Leaf venation.*—Pinnate, upper surface 147B, tinged 191A, lower surface 144B.

*Leaf size.*—Leaf; 15.3 cm in length and width, leaflet; 9.6 cm in length, 3.5 cm in width, base of leaf wings 2.6 cm in length, 1 cm in width.

*Leaf surface.*—Upper and lower surface glabrous, smooth, very slightly glossy.

*Leaf color.*—Young upper surface; 147B, veined 146B to 146C, young lower surface; 147A and N189A, mature upper surface; 143A and 143B, base of leaf wings 143B, mature lower surface; 147B, slightly tinged 191A, base of leaf wings 146A to 146B, heavily covered with fine dots 200C.

*Leaf attachment.*—Petiolate.

*Petioles.*—Strong, an average of 11 cm in length and 6 mm in diameter, both surfaces very slightly glossy, color; 144A, finely dotted and striped with 200C, more heavily towards the proximal end.

Inflorescence description:

*Inflorescence type.*—Solitary or in pairs.

*Lastingness of inflorescence.*—Freely flowering, sepals persistent, other parts self-cleaning, lasts an average of 10 days.

*Flower number.*—1 to 2 per plant.

*Flower fragrance.*—None.

*Flower aspect.*—Outward to slightly nodding.

*Flower size.*—Average of 7.5 cm in height and diameter, 2.5 cm in depth.

*Flower type.*—Rotate, slightly to moderately bowl-shaped, single.

*Flower buds.*—Ovate in shape, glabrous and matte surface, 2.2 cm in length, 1.2 cm in diameter, color; a blend of 145D and 157A, top NN155B.

*Peduncles.*—Strong, average of 9.1 cm in length, diameter at widest point 8 mm, diameter at narrowest point 7 mm, held in an average angle of 75°, glabrous and moderately glossy surface, 144A to 144B, tinged at nodes 178B, slightly covered with fine dots at the base 200C to 200D.

*Pedicels.*—Moderately strong, average of 4.2 cm in length, diameter at widest point 4 mm, diameter at narrowest point 3 mm, held in an average angle of 20°, glabrous and moderately glossy surface, 145A to 145B, base 178B.

*Petals.*—Petals are transformed into nectaries, rotate in arrangement, 17, 1 whorl, 8 mm in length, 4 mm in width, uneven tubular and flattened in shape, rounded tip, fused into tube, surfaces; slightly glossy, petals both surface glabrous, smooth, flower throat both surfaces glabrous, smooth, inside is covered in nectar, flower tube both surfaces glabrous, smooth, color; when opening upper surface 157A, longest side of the tube 150B, when opening lower surface 150B, proximal end 150A, when fully open upper surface 157C, longest side of the tube 154C, fading to 157C, longest side of tube 154C, when fully open lower surface 157C, longest side of the tube 154C, proximal end 144C, fading to 157C, longest side of tube 154B, proximal end 144B, flower throat; 154C, flower tube; shortest side of tube 157C, longest side of tube 154C, proximal end 144C.

*Calyx.*—Rotate, 2.5 cm in length, 7.5 cm in diameter.

*Sepals.*—Showy, rotate, 6 (varying between 5 and 7), 2 whorled rows, 4.4 cm in length, 3.9 cm in width, broadly ovate to slightly concave in shape, obtuse to broadly acute apex, broadly cuneate base, entire to moderately undulate margins, both surfaces glabrous, upper surface matte, lower surface very slightly glossy, color; upper surface when opening and fully open NN155B, slightly tinged 145C, base 145B, when opening lower side 155C and NN155B, slightly tinged 145C to 145D, base 145B, when fully open lower surface NN155C, base 145B.

*Bracts.*—1 or 2 held at each node, narrowly ovate in shape, 4.2 cm in length, 2.2 cm in width, entire margins, acute apex, occasionally cleft, cuneate base, color; upper surface NN137B, center and base 138A, lower surface 137C, center and base 144A.

Reproductive organs:

*Stamens.*—100, filaments; 1 cm in length, NN155D in color, anthers; basifixed, double broad kidney-shape, 2 mm in length, 1.75 mm in width, 154C to 154D in color, pollen; moderate and 155A in color.

*Pistils.*—Varying between 7 and 13, 6 mm in length, stigma; 0.3 mm in diameter, club-shaped, NN155B in color, style; 5.5 mm in length, NN155B in color, ovary; 155C in color.

It is claimed:

1. A new and distinct cultivar of *Helleborus* plant named 'GRUHEL02' substantially as herein illustrated and described.

* * * * *